US010675142B2

(12) United States Patent
Gregoire et al.

(10) Patent No.: US 10,675,142 B2
(45) Date of Patent: Jun. 9, 2020

(54) FIXATION DEVICE AND TISSUE FIXATION METHOD FOR ACL RECONSTRUCTION

(71) Applicant: MV N8TIVE, LLC, Marietta, GA (US)

(72) Inventors: David Gregoire, Mission Viejo, CA (US); George White, Corona, CA (US); Christopher Rodriguez, Costa Mesa, CA (US); Mark Harrold, Tranbuco Canyon, CA (US)

(73) Assignee: MV N8TIVE, LLC, Marietta, GA (US)

( * ) Notice: Subject to any disclaimer, the term of this patent is extended or adjusted under 35 U.S.C. 154(b) by 64 days.

(21) Appl. No.: 15/565,243

(22) PCT Filed: Apr. 7, 2016

(86) PCT No.: PCT/US2016/026340
§ 371 (c)(1),
(2) Date: Oct. 9, 2017

(87) PCT Pub. No.: WO2016/168045
PCT Pub. Date: Oct. 20, 2016

(65) Prior Publication Data
US 2018/0092735 A1    Apr. 5, 2018

Related U.S. Application Data

(60) Provisional application No. 62/188,255, filed on Jul. 2, 2015, provisional application No. 62/148,526, filed on
(Continued)

(51) Int. Cl.
*A61F 2/08*    (2006.01)
(52) U.S. Cl.
CPC ..... *A61F 2/0811* (2013.01); *A61F 2002/0823* (2013.01); *A61F 2002/0829* (2013.01);
(Continued)

(58) Field of Classification Search
CPC ......................................................... A61F 2/08
(Continued)

(56) References Cited

U.S. PATENT DOCUMENTS 6,517,578 B2    2/2003  Hein
6,554,862 B2 *  4/2003  Hays ..................... A61F 2/0811
                                                    623/13.11
(Continued)

FOREIGN PATENT DOCUMENTS

DE        9210543        1/1992
WO        2007109280     9/2007

OTHER PUBLICATIONS

ISR/WO of International PCT Application No. PCT/US2016/026340 dated Jul. 21, 2016.
(Continued)

*Primary Examiner* — Suzette J Gherbi
(74) *Attorney, Agent, or Firm* — FisherBroyles, LLP; Keats A. Quinalty

(57) ABSTRACT

A tissue fixation device for securing soft tissue to bone includes an expandable outer sheath, and an inner screw in threaded cooperation with the sheath. The expandable sheath comprises opposing walls in hinged engagement. When the screw is inserted into in the sheath, the walls pivot outwardly about a distal hinge to compress a tissue graft against the bone hole, and to lock the device therein. An optional cortical button is secured across the bone hole entrance, and tethered to the fixation device to bolster fixation.

13 Claims, 23 Drawing Sheets

Related U.S. Application Data on Apr. 16, 2015, provisional application No. 62/148,300, filed on Apr. 16, 2015.

(52) U.S. Cl.
CPC ............... *A61F 2002/0858* (2013.01); *A61F 2002/0882* (2013.01)

(58) Field of Classification Search
USPC ........................................ 623/13.11–13.19
See application file for complete search history.

(56) References Cited

U.S. PATENT DOCUMENTS

| | | | | |
|---|---|---|---|---|
| 7,329,281 B2* | 2/2008 | Hays | ............... | A61F 2/0811 606/232 |
| 7,611,540 B2* | 11/2009 | Clifford | ............. | A61B 17/7028 623/20.21 |
| 7,655,041 B2* | 2/2010 | Clifford | ............. | A61B 17/7028 623/13.12 |
| 7,967,861 B2* | 6/2011 | Montgomery | ........ | A61F 2/0811 623/13.14 |
| 10,231,823 B2* | 3/2019 | Piccirillo | ............... | A61F 2/0811 |
| 2004/0024456 A1* | 2/2004 | Brown, Jr. | ......... | A61B 17/0401 623/13.15 |
| 2004/0267361 A1* | 12/2004 | Donnelly | ............... | A61F 2/0811 623/13.14 |
| 2007/0233151 A1 | 10/2007 | Chudik | | |
| 2014/0172095 A1 | 6/2014 | Graf et al. | | |

OTHER PUBLICATIONS

European Examination Report for Application No. 16718568.5-1124 dated Aug. 14, 2019.

\* cited by examiner

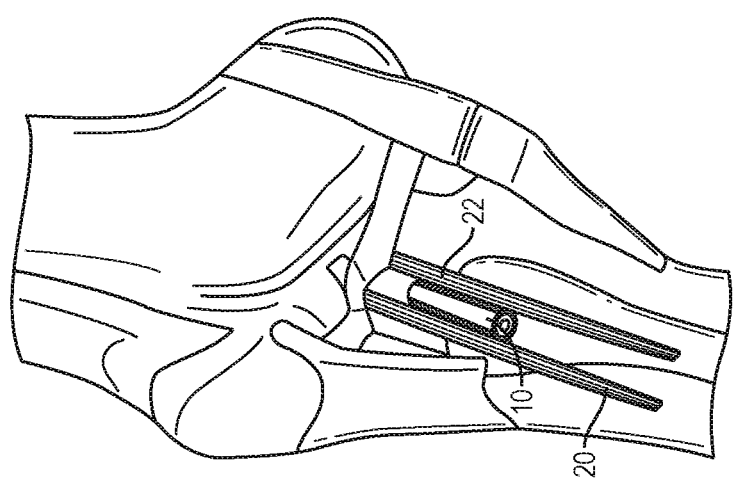

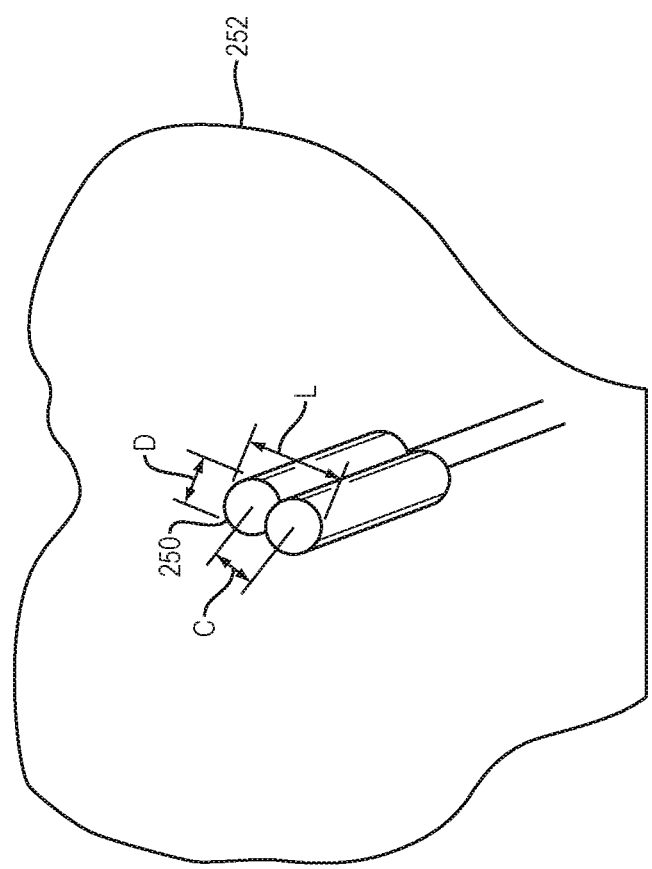

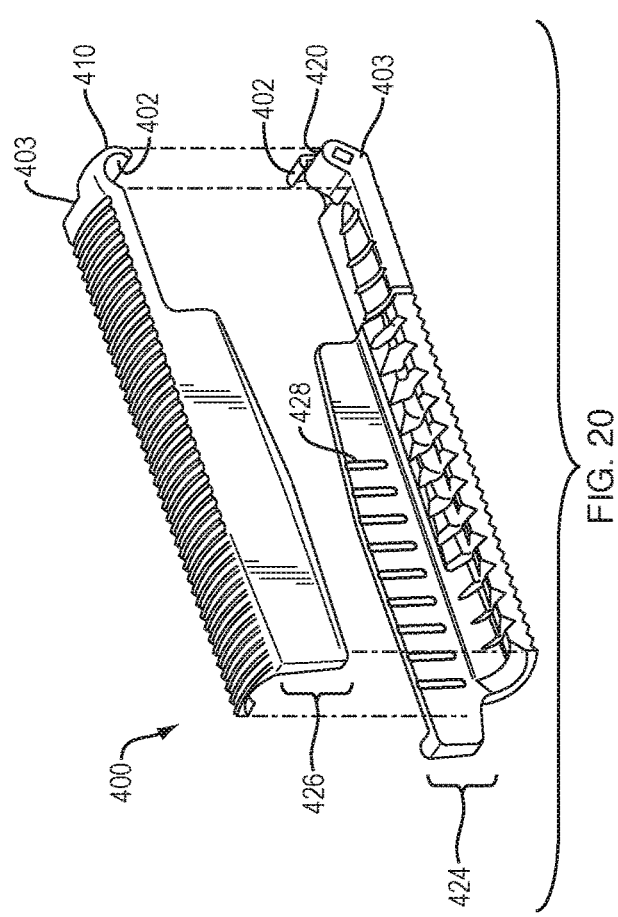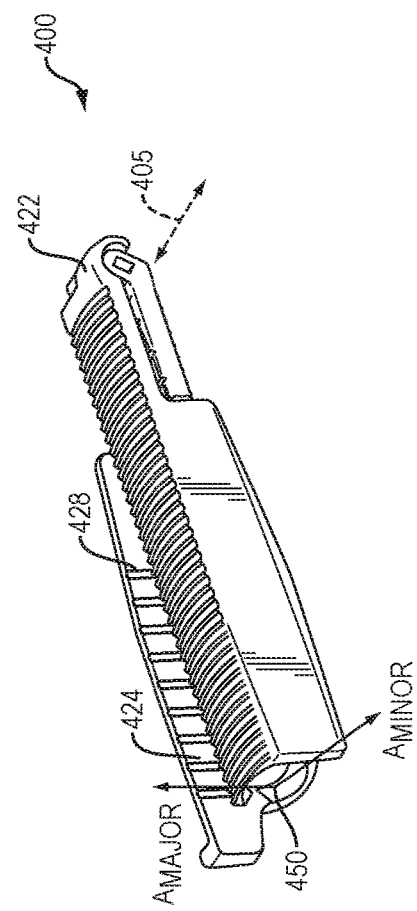

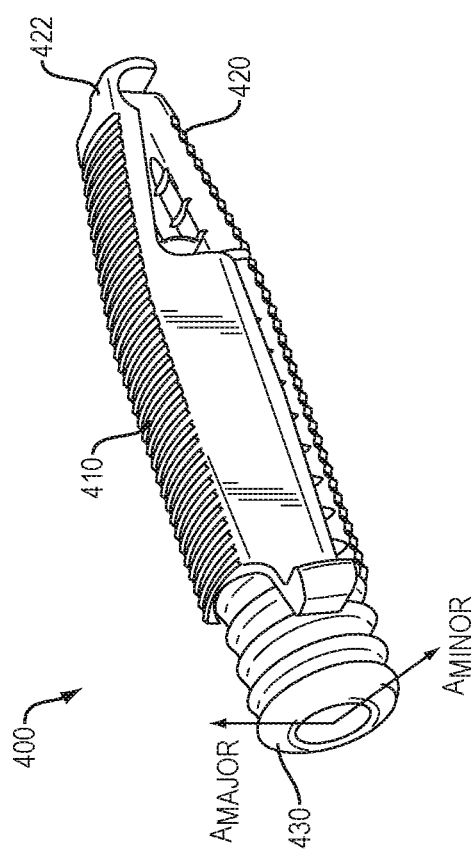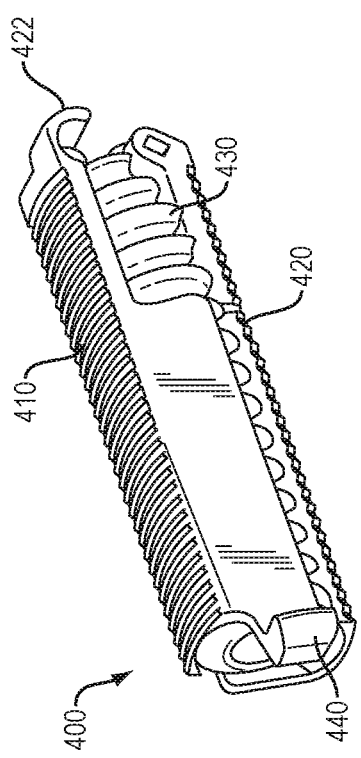
FIG. 22
FIG. 23

FIXATION DEVICE AND TISSUE FIXATION METHOD FOR ACL RECONSTRUCTION

CROSS-REFERENCE TO RELATED APPLICATIONS

This application is the U.S. national phase entry under 35 U.S.C. § 371 of International Application No. PCT/US2016/026340, filed Apr. 7, 2016, entitled "FIXATION DEVICE AND TISSUE FIXATION METHOD FOR ACL RECONSTRUCTION," which claims priority to and benefit of U.S. Provisional Application No. 62/148,300, filed Apr. 16, 2015, 62/148,526, filed Apr. 16, 2015, and 62/188,255, filed Jul. 2, 2015, the contents of which are incorporated herein by reference in their entirety for all purposes.

FIELD

This disclosure is directed to securing soft tissue to bone and, more particularly, to tissue fixation devices for securing soft tissue to bone for anterior cruciate ligament (ACL) reconstruction.

BACKGROUND

In an ACL procedure, soft tissue, such as a ligament graft, is affixed to the femur and the tibia. The tissue graft is implanted by securing one end of the tissue graft through a passage formed in the femur, and the other end of the graft through a passage formed in the tibia. Generally, a fixation device (e.g., an interference screw) is used to affix each end of the tissue graft to the bone.

A number of devices are commercially available to affix the graft to the bone. For example, the IntraFix ACL® Tibial Fastener System (manufactured by DePuy Synthes, a Johnson & Johnson Company, Warsaw, Ind., USA) features a two-part system including an expandable polypropylene sheath that receives a PEEK screw. The sheath expands and holds the graft in place as the screw is inserted into the sheath. The IntraFix® system attempts to more accurately replicate the native ACL by using a screw to spread apart an integral four quadrant sheath. This acts to compress the four tendon strands against the bone. The system may be considered by some to be easier to use than other alternatives, and does not need additional drill holes. However, the IntraFix® device does require additional accessories, additional people to perform the procedure, and the four quadrant design does not accommodate certain grafts with two tendon strands, such as the tibialis.

Various patents describe devices to affix the graft to bone. For example, U.S. Pat. No. 7,309,355 to Donnelly et al. describes a radially expandable sheath having a substantially closed distal end with at least two sidewalls extending proximally therefrom and defining a central lumen. Each sidewall can have a substantially concave outer surface adapted to seat a graft member, and each side wall is at least partially separated by a longitudinally oriented slot that extends from a proximal end along a substantial length of each sidewall. The slot preferably terminates at a position just proximal to the distal end. The device can also include a sheath expander that is adapted to be disposed in the central lumen of the radially expandable sheath configured to flex the sidewalls to radially expand the sheath so as to fix a graft member within a bone tunnel.

U.S. Pat. No. 8,562,680 to Hays et al. describes another radially expandable sheath. In the '680 patent, a graft ligament anchor comprises a graft ligament engagement member disposed in an opening in a bone. The graft ligament engagement member is arranged to receive a graft ligament alongside the engagement member and a locking member for disposition in the opening, and is at least in part engageable with the graft ligament engagement member. Movement of the locking member in the opening causes the locking member to urge the engagement member, and the graft ligament therewith, toward a wall of the opening to secure the graft ligament to the wall of the opening.

US Publication No. 2012/0109299 to Li et al. describes another system and method for ligament reconstruction including an implant having a sheath, a first ledge, a second ledge, a first anchor and a second anchor. The sheath has an exterior surface and an interior surface, wherein the interior surface of the sheath forms a lumen configured to receive a sheath expander. The first ledge and the second ledge are configured to separate the ligaments and act as an anchor for the sheath in the bone tunnel. The first anchor and the second anchor are configured to engage the ligaments and be expandable outwards away from the lumen to provide fixation in a bone tunnel. When the implant receives the sheath expander, the ligaments can be separated, positioned, and secured in the bone tunnel.

U.S. Pat. No. 8,663,325 to Graf et al. describes another soft tissue graft anchor including a plurality of prongs. Each prong includes a distal end and a proximal end, wherein the prongs are coupled at their distal ends to form an inner cavity having an opening. At least one of the prongs includes a fin. The fin extends perpendicular to a longitudinal axis of the prong and includes a pointed end. A tissue graft anchor assembly, a method for tissue repair, and instrumentation for use therewith is also disclosed.

The above mentioned devices generally rely on the elasticity of the sheath walls to deform. The wall material must have a relatively high elasticity. The wall must also predictably bend in situ when the inner screw member is deployed to expand into the graft.

U.S. Pat. No. 7,967,861 to Montgomery et al. describes another expandable sheath for affixing tissue to bone. The '861 patent describes a material fixation system which comprises two sheath portions defining a space therebetween, and a hinge for attaching the sheath portions together along one side thereof. An insertion member, preferably a tapered screw, is insertable into the space for expanding the sheath portions laterally outwardly in order to urge a soft tissue graft against an adjacent bone surface. Although the '861 patent does include a hinge for opening two sheath portions against the graft legs, the side position of the hinge is not optimal because it may cause a shearing force on the graft legs in addition to a compression force.

The above mentioned devices can be improved to more reliably secure the soft tissue in a bone. This is especially important concerning the tibia because the tibial side becomes the weakest link in the reconstructed anatomy. Furthermore, there is no back up fixation in the event the tibia side fails.

SUMMARY

Described herein are tissue fixation systems, devices, and methods for securing soft tissue to bone which advantageously provides uniform compression along the graft, backup (or redundant) fixation, higher pull-out strength, and ease of deployment. The systems described herein provide at least two modes of fixation, including a first tunnel-lock mode, and a second outer cortical-layer mode. Both modes of tissue fixation provide a force that opposes the tissue pull out.

In embodiments, a fixation device for securing a soft tissue in a bone hole includes a screw with external surface features, a sheath having a proximal end, a distal end, and a lumen extending from the proximal end towards the distal end, the lumen having internal surface features to receive and engage the external surface features of the screw. The sheath also has a first sheath component having a first side wall and a first lateral wall, a second sheath component non-integrally formed with the first sheath component, and the second sheath component having a second side wall and a second lateral wall. The lumen is defined by the first side wall, the second side wall, the first lateral wall, and the second lateral wall. The first sheath component and the second sheath component are in hinged engagement about a lateral axis at the distal end of the sheath, enabling the first lateral wall to incrementally pivot from the second lateral wall about the lateral axis according to the depth that the screw is inserted into the lumen of the sheath.

In embodiments, the fixation device has an outer diameter that decreases from the proximal end to the distal end, and the fixation device has an inner diameter that decreases from the proximal end to the distal end.

In embodiments, the first side wall and the second side wall are substantially flat or are substantially parallel. In embodiments, the first side wall and the second side wall have internally disposed vertical guides.

In embodiments, the first lateral wall and second lateral wall have curved internal surfaces. In embodiments, the first lateral wall and the second lateral wall each have an exterior surface to contact the tissue, and the exterior surface having surface features to grip the tissue when the sheath is deployed.

In embodiments, the fixation device further includes a nub member at the proximal end of the sheath to engage an exterior surface of the bone, thereby limiting the depth of insertion of the sheath into the bone hole.

In embodiments, the fixation device further includes at least one longitudinally disposed seam extending from the proximal end to the distal end of the sheath, said seam separating the first sheath component from the second component.

In embodiments, a fixation device for securing a soft tissue in a bone hole includes a screw and a sheath having a first part, a second part non-integral to the first part, a proximal end, a distal end, a lumen extending from the proximal end to the distal end and adapted to accept the screw, and a hinge rotatably interlocking the first part to the second part at the distal end. The lumen has a longitudinal axis extending from a proximal end to the distal end of the sheath, and a cross section comprising a lateral dimension and a vertical dimension. The sheath further includes a first low profile configuration when the sheath is inserted into the bone hole, and a second high profile configuration when the sheath is deployed in the bone hole to lock the tissue therein. The second high profile configuration is assumed when the screw is inserted into the lumen, causing the lumen to substantially enlarge in the vertical dimension while the lateral dimension remains substantially the same, thereby causing an exterior surface of the sheath to be urged against the tissue and locking the tissue in the bone hole.

In embodiments, the hinge includes substantially rigid discrete separable elements, thereby causing the first part of the sheath to disengage from the second part of the sheath when the screw is inserted a predetermined depth.

In embodiments, each of the first part and the second part of the sheath have a vertical wall. In embodiments, a portion of each vertical wall extends beyond the vertical dimension of the sheath when the sheath is in the first low profile configuration.

In embodiments, the fixation device further includes a cortical button tethered to a proximal end of at least one of the screw and the sheath, the cortical button having at least one barb to engage the cortical surface of the bone. In embodiments, the cortical button further includes an interlocking feature to register with a corresponding interlocking feature present on the sheath.

In embodiments, the fixation device includes any one or more of the components recited herein.

In embodiments, a fixation device for securing a soft tissue in a bone hole includes an outer expandable sleeve, an inner screw, and a cortical button tethered to at least one of the screw and the sleeve.

In embodiments, a fixation device for securing a soft tissue in a bone hole includes an outer spacer, and a separable hinge.

In embodiments, a fixation system for securing a soft tissue in a bone hole includes a sleeve insertion instrument and sleeve attached thereto, and a screw insertion instrument and screw attached thereto.

In embodiments, a fixation system for securing a soft tissue in a bone hole, the bone hole having an noncircular-shaped cross section, a major axis, and a minor axis, includes an insertion instrument, an expandable sleeve detachably secured to the insertion instrument, the expandable sleeve having a lumen extending from a proximal end to a distal end of the sleeve, the lumen decreasing in diameter from the proximal end to the distal end of the sleeve, and a screw detachably secured to the insertion instrument. The screw has a distal tip, and a taper decreasing in diameter towards the distal tip such that when the screw is inserted into the lumen of the expandable sleeve, the lumen expands in a vertical direction and a lateral direction, the vertical direction and the lateral direction corresponding to the major axis and the minor axis respectively of the bone hole. The sleeve expands more in the vertical direction than the lateral direction as the screw is inserted, thereby providing a substantially uniform force to the soft tissue in the vertical direction from the distal end to the proximal end of the sleeve.

In embodiments, the fixation system further includes a seam separating the sheath into at least a first component and a second component non-integral with the first component.

In embodiments, the fixation system further includes a multi-element hinge disposed at the distal end of the sheath, such that the first component pivots relative to the second component when the screw is inserted in the lumen.

In embodiments, the fixation system further includes a cortical button tethered to at least one of the sleeve and the screw.

In embodiments, a reconstruction method to affix a soft tissue to bone includes performing any one or more of the steps described herein.

In embodiments, a reconstruction method to affix a soft tissue to a non-circular bone hole, the bone hole having side walls, a top wall, and a bottom wall, the side walls being larger than the top wall and the bottom wall, and the soft tissue having a top leg and a bottom leg, and the top leg being disposed between the top wall and an expandable sleeve, and the bottom leg being disposed between the bottom wall and the expandable sleeve, includes: 1) enlarging the expandable sleeve in a lateral direction such that an exterior surface of the expandable sleeve makes direct contact with the side walls of the bone hole, and 2) enlarging the expandable sleeve in a vertical direction. The enlarging the expandable sleeve in the vertical direction is greater than the enlarging the expandable sleeve in the lateral direction, thereby causing the top leg of the soft tissue to be compressed between the top wall of the bone hole and the expandable sleeve, and the bottom leg of the soft tissue to be compressed between the bottom wall of the bone hole and the expandable sleeve, and for the expandable sleeve to be firmly secured in the bone hole. The step of enlarging the expandable sleeve in the vertical direction is performed by pivoting a first component relative to a second component of the expandable sleeve.

In embodiments, the steps of enlarging are performed simultaneously by inserting a screw into a lumen of the expandable sleeve.

In embodiments, the pivoting is about a hinge structure located at the distal end of the sleeve, the hinge structure being formed by a plurality of discrete elements.

In embodiments, the reconstruction method further includes separating the expandable sleeve into at least two components by continuing to insert the screw into the sleeve to a predetermined depth thereby causing the hinge structure to separate, and to continue to maintain compression force on the soft tissue.

In embodiments, enlarging the expandable sleeve in the lateral dimension is performed by elastic deformation of the expandable sleeve.

Still other embodiments should become apparent from the detailed description to follow along with the accompanying drawings.

BRIEF DESCRIPTION OF THE DRAWINGS

Objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIGS. 1-3 illustrate installing a fixation device in the tibia to secure a tissue graft thereto;

FIGS. 11-15 illustrate installing another expandable fixation device and cortical component to secure a tissue graft to the tibia;

FIGS. 20-23 are various views of another fixation device comprising a hinged sleeve and interference screw;

DETAILED DESCRIPTION

Figure 1:
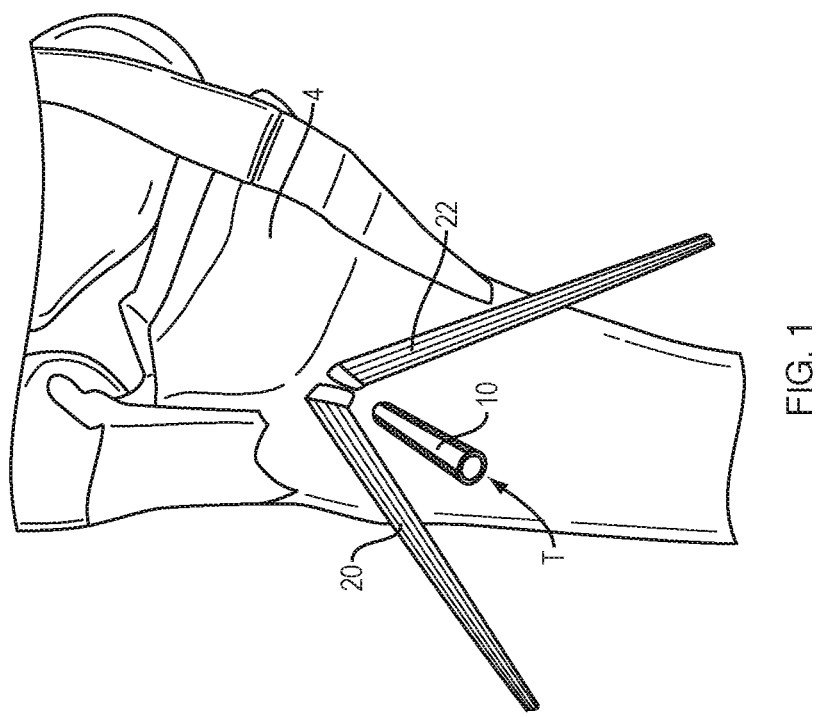

The description, objects and advantages of the present disclosure will become apparent from the detailed description to follow, together with the accompanying drawings.

Before the present disclosure is described in detail, it is to be understood that this disclosure is not limited to particular variations set forth herein as various changes or modifications may be made to the disclosure described and equivalents may be substituted without departing from the spirit and scope of the disclosure. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. In addition, many modifications may be made to adapt a particular situation, material, composition of matter, process, process act(s) or step(s) to the objective(s), spirit or scope of the present disclosure. All such modifications are intended to be within the scope of the claims made herein. In the description that follows, like components have been given the same reference numerals, regardless of whether they are shown in different examples.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the disclosure. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present disclosure (in which case what is present herein shall prevail). The referenced items are provided solely for their disclosure prior to the filing date of the present application. Nothing herein is to be construed as an admission that the present disclosure is not entitled to antedate such material by virtue of prior disclosure.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Last, it is to be appreciated that unless defined otherwise, all technical and scientific terms used herein have the same meaning as commonly understood by one of ordinary skill in the art to which this disclosure belongs.

Figure 3:
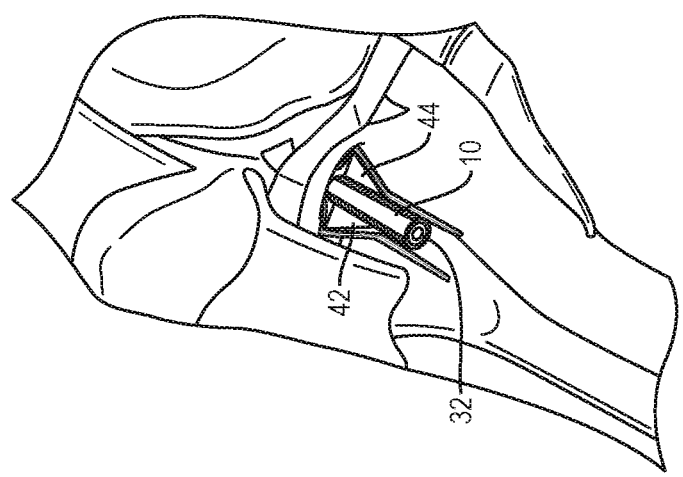

Turning now to the figures, FIGS. 1-3 illustrate one technique for securing soft tissue to a bone, such as a tibia 4. First, tissue graft bundles 20, 22 are pulled to a desired tension, either manually or with tensioner. A tissue fixation device 10, examples of which are further described below, is lightly tapped (T) into a bone hole, preferably a tapered and noncircular cross section hole, as further described below. The fixation device 10 is shown as having a taper. The taper of the fixation device 10 matches the taper of the bone hole. Thus, the fixation device 10 can be pressed deeper for additional fixation if desired.

With reference to FIG. 2, the fixation device 10 is shown inserted into the bone hole, and separating the two graft bundles 20, 22. FIG. 3 shows an interference screw 32 inserted into the fixation device 10, deploying active lock wings 42, 44 on the fixation device 10 as further described below. This action compresses the graft bundles 20, 22 (FIG. 2) against the wall of the bone hole. The fixation device 10 also expands radially against the side walls of the bone hole. The ends of the graft bundles 20, 22 are then trimmed.

Figure 4:
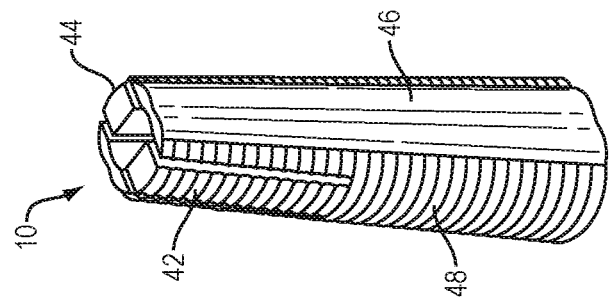
FIG. 4 is a perspective view of an outer component of the fixation device shown in FIGS. 1-3 in an unexpanded profile.

FIG. 4 is an enlarged perspective view of an example of a tissue fixation device 10 as used in the method of FIGS. 1-3. Expanding wings 42, 44 are shown towards the distal end of the fixation device 10 in an undeployed state. The wings 42, 44 are shown integrally connected to a body 46. When the fixation device 10 is inserted into a bone hole, the wings 42, 44 deflect or deform outwards from the body 46. Surface features such as barbs or ridges 48 are shown on the body 46 and the wings 42, 44. The ridges 48 serve to grip the fixation device 10 into tissue and bone.

Figure 5:
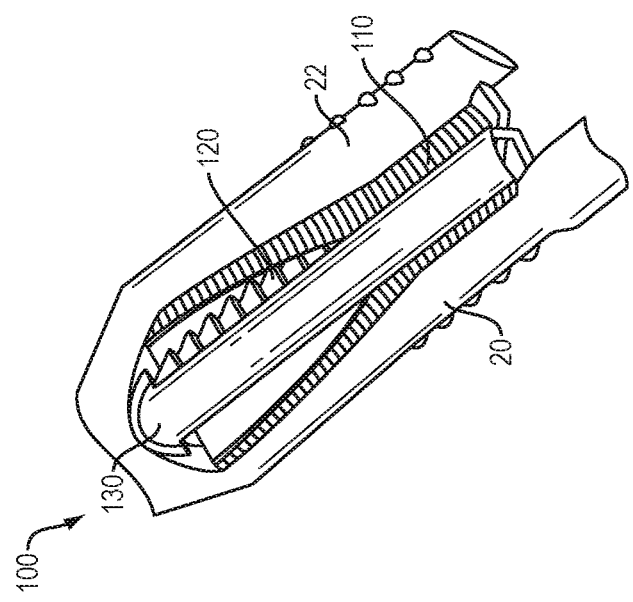
FIG. 5 is an illustration of another fixation device securing a tissue graft in a bone hole in the tibia.

FIG. 5 is an illustration of another tissue fixation device 100. Fixation device 100 includes a shell 110 and an interference screw 120. The fixation device 100 is shown in an expanded profile, holding graft bundles 20, 22 in a bone hole. The shell 110 terminates in a blunted or rounded distal tip 130. The distal tip 130 atraumatically accommodates the graft bundles 20, 22 where the graft bundles 20, 22 change direction so that each leg of the graft bundles 20, 22 may extend along opposite sides of the shell body 110.

Figure 6:
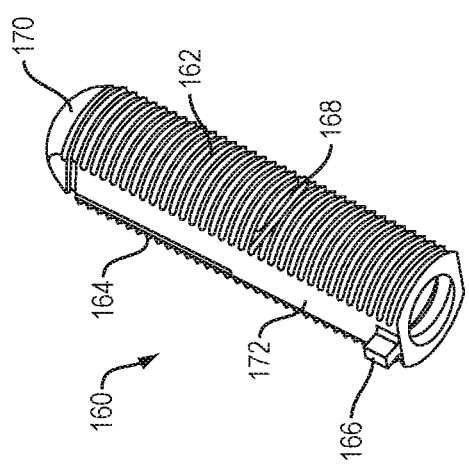
FIGS. 6-7 are various views of another outer component of a fixation device in an unexpanded profile.
Figure 7:
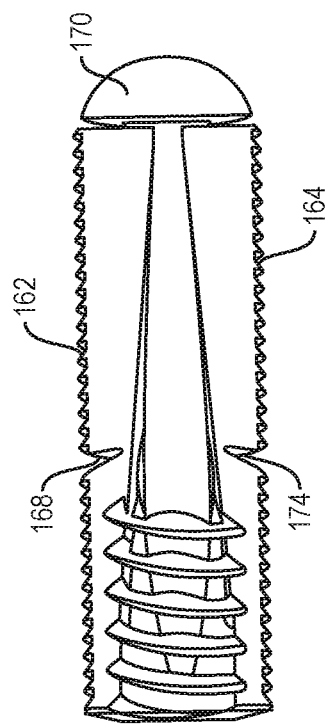

FIGS. 6-7 illustrate another tissue fixation device 160 comprising expanding arms 162, 164. The expanding arms 162, 164 are deflected from the body 172 about joints 168, 174. A nub 166 is also shown to limit insertion depth of the tissue fixation device 160 into the bone hone. A tip 170 is gently curved to accommodate the graft bundles (not shown) being placed across the tip 170.

Figure 10:
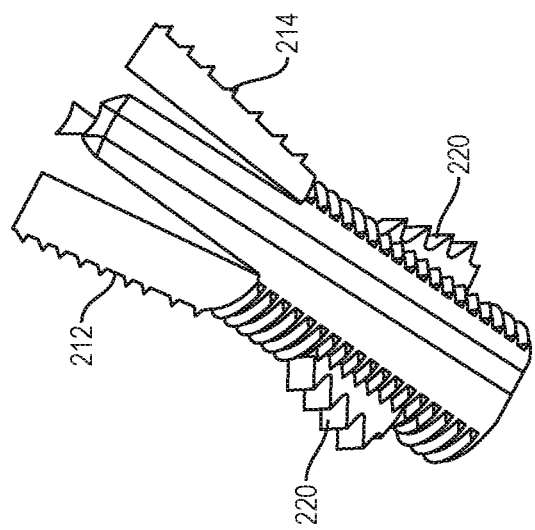
FIG. 10 is a perspective view of the outer component shown in FIGS. 8-9 in an expanded profile.
Figure 9:
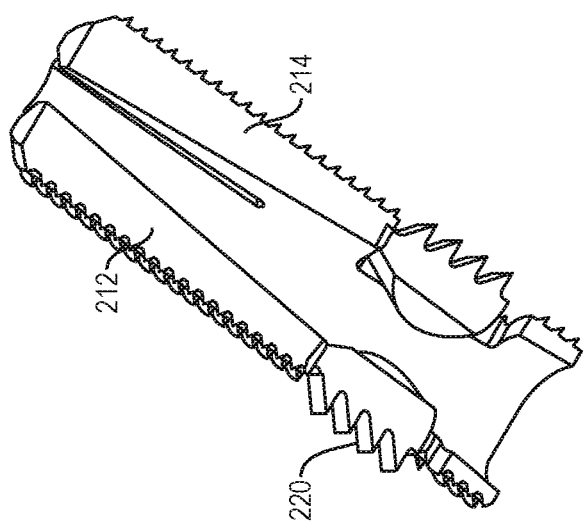
FIGS. 8-9 are cross sectional views of another outer component of a fixation device in an unexpanded profile.
Figure 8:
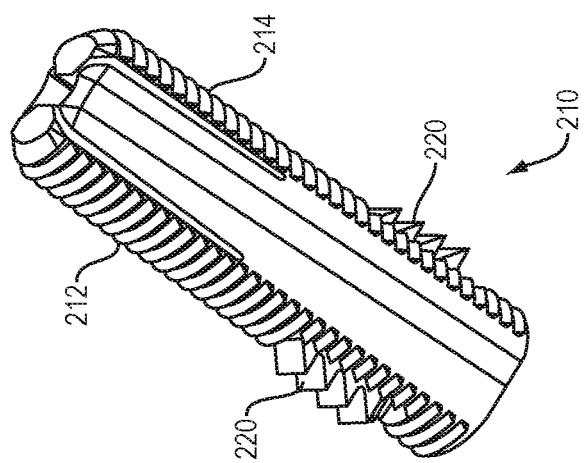

FIGS. 8-10 illustrate another tissue fixation device 210 comprising distal expanding arms 212, 214. The tissue fixation device 210 is also is shown as having a proximal enhanced ridge area 220. The enhanced ridge area 220 facilitates locking with the bone walls and/or graft bundles along a proximal region of the bone tunnel. FIG. 10 shows the tissue fixation device 210 in an expanded profile, with the anatomy removed for clarity.

FIGS. 11-15 illustrate another technique for securing soft tissue to bone by use of a button or planar cap. The button snugly fits on top of (namely, covers) the bone hole, as further described below.

As shown in FIG. 11, a noncircular bone hole 250, which may be in the form of two overlapping circles (or figure eight), is first created in the bone, e.g., a tibial head 252. Noncircular bone holes may be created using a guide and drill as described in, e.g., U.S. Pat. Publication 2010/0249930 to Myers. A diameter (D) of the largest cross-sectional portion of the bone hole may be about 6.5 mm to about 8.0 mm. A length (L) from a first end to a second end of the bone hole may be about 12.5 mm to about 14.0 mm. A distance (C) from a center of the first overlapping circle to a center of the second overlapping circle may be about 6.0 mm to about 6.5 mm.

Figure 12:
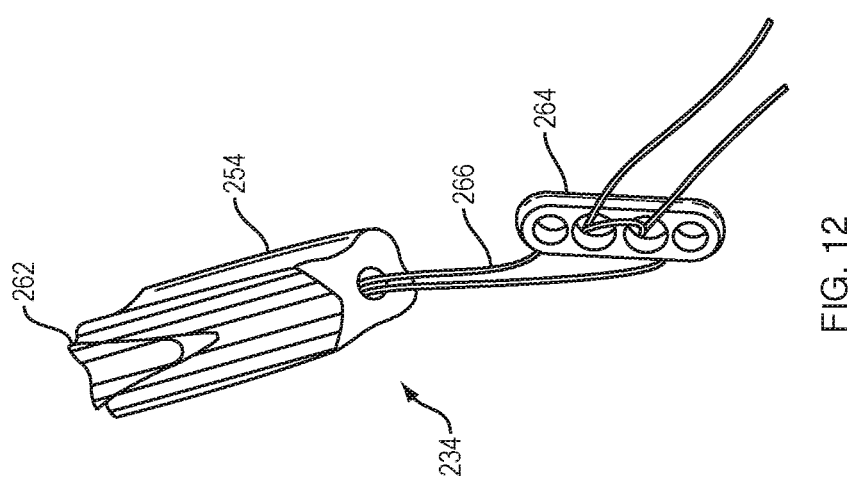

FIG. 12 shows a tissue fixation system comprising a tissue fixation device 234 and a cortical button 264. The tissue fixation device 234 is similar to the tissue fixation devices 10, 100, 160 and 210 described herein and generally includes an outer shell member 254 and an inner screw member 262. The tissue fixation device 234 is installed inside the bone hole 250 (FIG. 11), and presses the graft bundle (not shown) against the walls of the bone hole 250. The cortical button 264 is attached with a suture 266 to the tissue fixation device 234 via a cinchable (or closable) cradle loop. The cortical button 264 serves to provide additional tissue fixation, as further described below. Non-limiting examples of cortical buttons and associated cradle loop assemblies are shown and described in U.S. Pat. No. 6,517,578 to Hein, and in the Endobutton family of products (manufactured by Smith & Nephew, Inc., Andover, Mass., USA).

Figure 13:
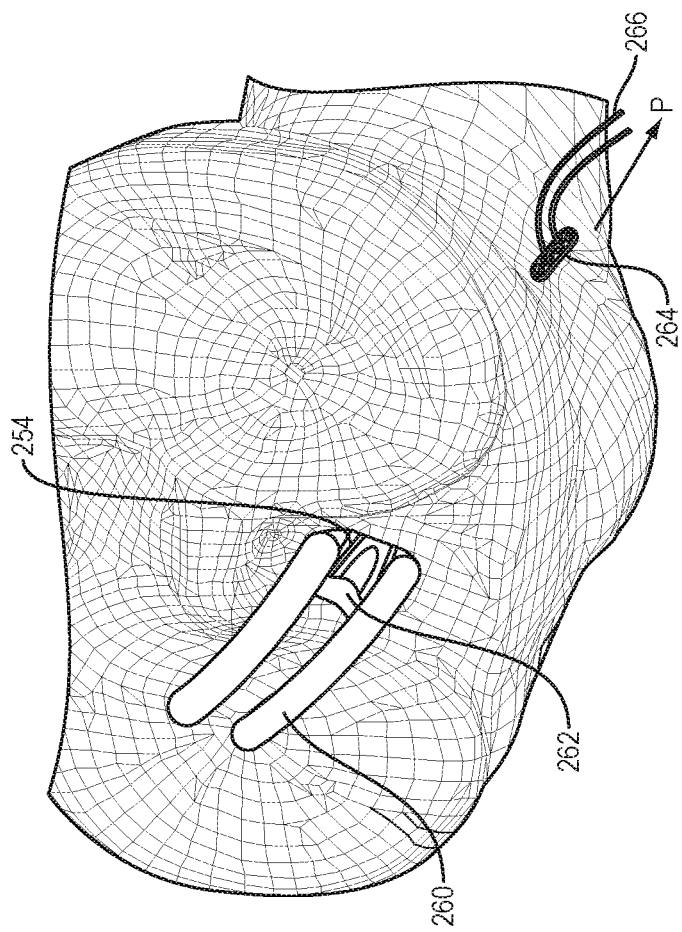

With reference to FIG. 13, the tendon 260 is wrapped around the outer shell 254 member and pulled (P) into the joint through an AM portal. The tendon 260 is pulled into the bone hole 250, and the cortical button 264 is shown pulled in the direction (P), and exiting the bone hole 250. Inner screw member 262 of the tissue fixation device 234 is forced against the outer shell member 254, creating expansion and pressing the tendon 260 against the walls of the bone hole 250.

Figure 14:
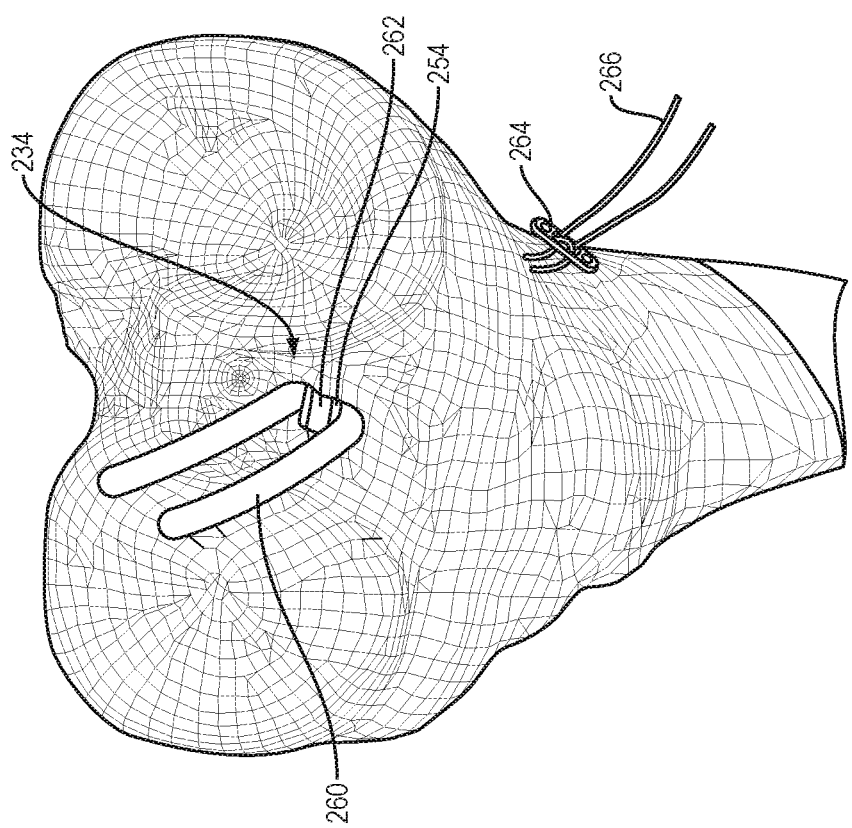
Figure 15:
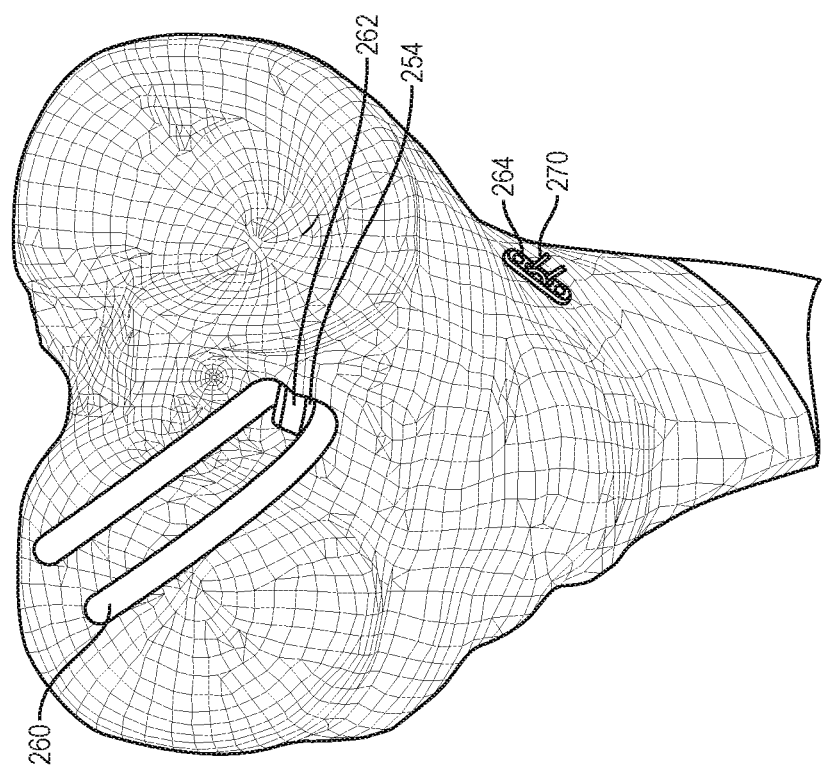

FIG. 14 shows the tissue fixation device 234 fully deployed and locked in the bone hole. The cortical button 264 is pulled snug to the cortex of the bone as a backup or ancillary fixation. The cortical button 264 is disposed flat or planar against the surface of the bone. The cortical button 264 supplements the fixation of the outer shell member 254 fixation via the tensioned sutures 266. FIG. 15 shows the suture limbs 270 trimmed. The tissue fixation is now complete.

Figure 16:
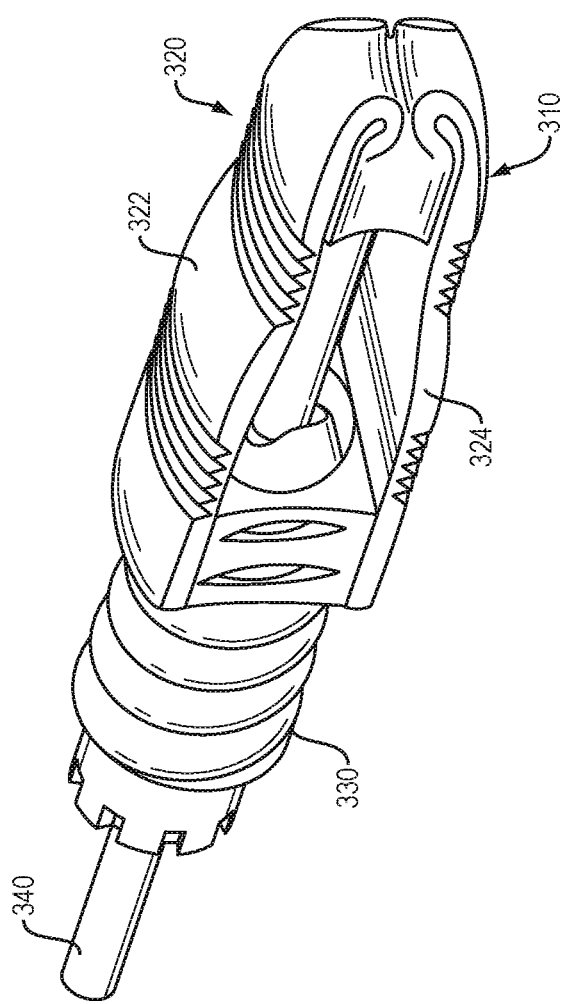
FIGS. 16-19 are various views of another fixation device comprising an expandable spacer, interference screw, and insertion stem.
Figure 17:
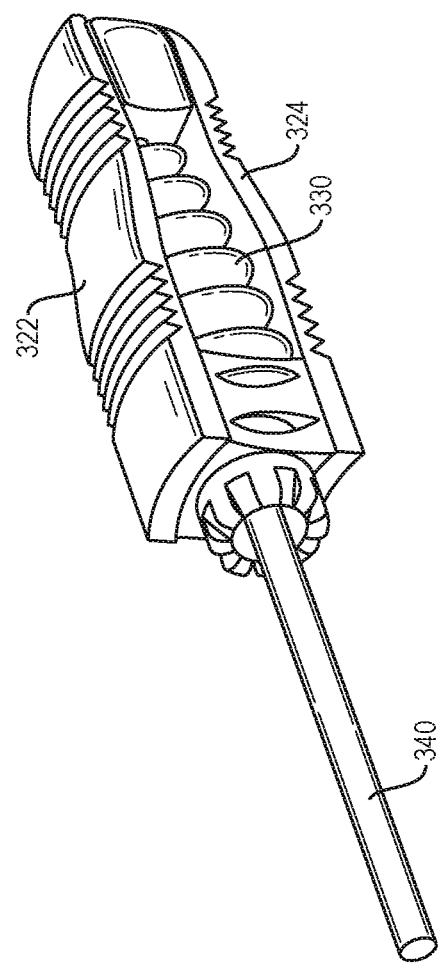
Figure 18:
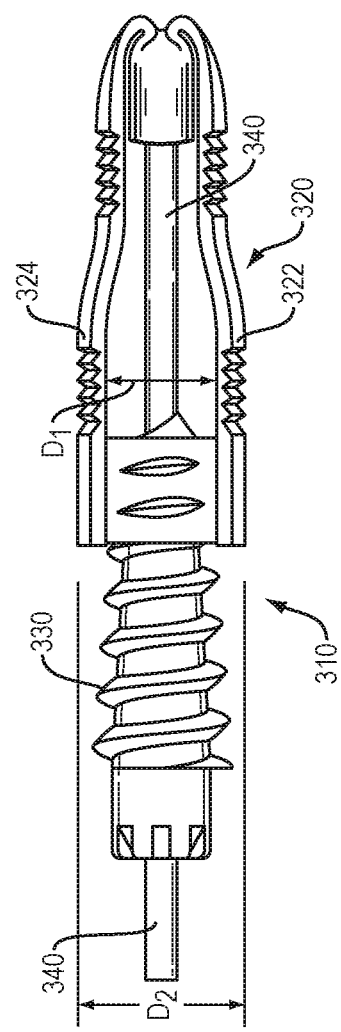

FIGS. 16-18 are various views of another tissue fixation device 310. The tissue fixation device 310 is shown having an expandable spacer 320 and an interference screw 330 movably coupled to the expandable spacer 320 by, for example, cooperating threads. The expandable spacer 320 is shown having expanding arms 322, 324. The inner diameter ($D_1$) (FIG. 18) between the two arms 322, 324 is selected to be smaller than the outer diameter ($D_2$) of at least a portion of the interference screw 330. In embodiments, the inner diameter ($D_1$) of the expandable spacer 320 is tapered toward the distal end. The expandable spacer 320 is expanded by insertion of the interference screw 330 into the spacer 320. As the interference screw 330 is inserted, the arms 322, 324 expand and provide ligament/tendon compression against the bone hole. An optional insertion stem 340 is shown connected to the spacer 320. The stem 340 serves to guide or direct the interference screw 330 during insertion and maintain the interference screw 330 screw on track. The stem 340 may be removed after the procedure is complete.

Figure 19:
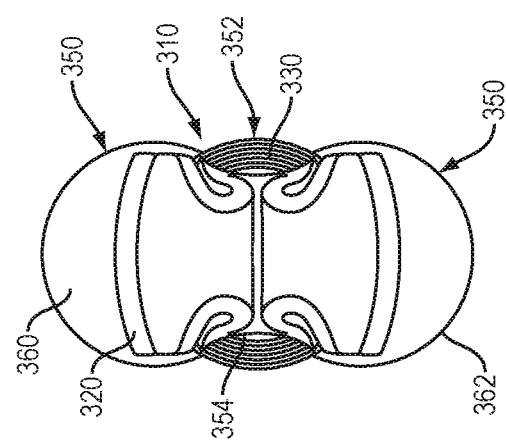

FIG. 19 is an end view showing the tissue fixation device 310 inserted into a noncircular bone hole 350 constructed in bone. Bone hole 350 is shown having an elongated (or figure eight) cross section. Ridges or threads 352 on the interference screw 330 contact the narrowed region or neck 354 of the bone hole 350, while the tendon or graft tissue 360 contacts the wider region 362 of the bone hole 350. Thus, the tissue fixation device 310 provides a cortical lock between the bone hole 350 and the interference screw 330. When not expanded, the spacer 320 is easily inserted in the bone hole 350 without compressing the tissue to the bone hole 350. Then, as shown in FIG. 19, expansion of the spacer 320 after insertion of the interference screw 330 provides ligament/tendon 360 compression against the bone hole 350.

FIGS. 20-23 illustrate another expandable tissue fixation device 400. In FIGS. 20-21, tissue fixation device 400 is shown with first and second elongated sheath members 410, 420. The sheath members 410, 420 are rotatably joined at a distal hinge 422. The sheath members 410, 420 may be provided in a collapsed low profile configuration such that the tissue fixation device 400 is handled and inserted into a bone hole as one assembly. Hinge 422 is shown comprising multiple elements including a socket 402 and a pin 403 which is rotatably held in the socket 402. Each sheath member 410, 420 of the tissue fixation device 400 may include a socket 402 and a pin 403. The multi-element hinge design promotes rotation about a lateral axis 405. Additionally, each hinge 422 element may be substantially rigid or firm. The hinge 422 is effective and accurate and does not rely on a degree of flexure or elasticity in the material such as a living hinge design.

In FIGS. 20-21, sheath members 410, 420 are also shown having side wall portions 424, 426. That is, sheath member 410 comprises side wall portion 426, and sheath member 420 comprises side wall portion 424. The sheath members 410, 420, together with the side wall portions 424, 426, define a lumen 450, which may be tapered from a proximal to a distal end. Side wall portions 424, 426 extend vertically and are parallel to the major axis ($A_{major}$) of the bone hole after insertion of the tissue fixation device 400 into the bone hole. The side wall portions 424, 426 may be substantially flat, or may have a curved inner surface. Surface features, such as vertical legs 428 on the inner side wall portions 424, 426, serve to guide mating surface features of the screw 430, such as threads, prohibiting the screw 430 from tracking off the longitudinal axis of the bone hole and into the bone.

FIG. 21 shows the sheath members 410, 420 in a collapsed configuration for easy insertion into a bone hole. The side wall portions 424, 426 of the sheath members 410, 420 extend beyond the vertical dimension of the lumen 450 when in the collapsed configuration. FIGS. 22-23 shows insertion of a screw 430 into the tissue fixation device 400. Like the lumen 450, the screw 430 may be tapered from a proximal to a distal end. As the screw 430 is inserted into the tissue fixation device 400, the first and second sheath members 410, 420 pivot away from one another about distal hinge 422, thereby enlarging the tissue fixation device 400. The sheath members 410, 420 continue to pivot from one another as the screw 430 is inserted until the distal hinge 422 separates into discrete elements. The hinge 422 releases and each sheath member 410, 420 spreads outward along the major axis ($A_{major}$) of the bone hole. Distal spreading of the sheath members 410, 420 provides fixation of the graft against the walls of the bone hole along its major axis (namely, the wide region). FIG. 23 also shows a cortical nub 440 (positioned near or along the minor axis of the bone hole) on the tissue fixation device 400. The cortical nub 440 limits the depth that the tissue fixation device 400 is inserted into the bone hole.

Figure 24:
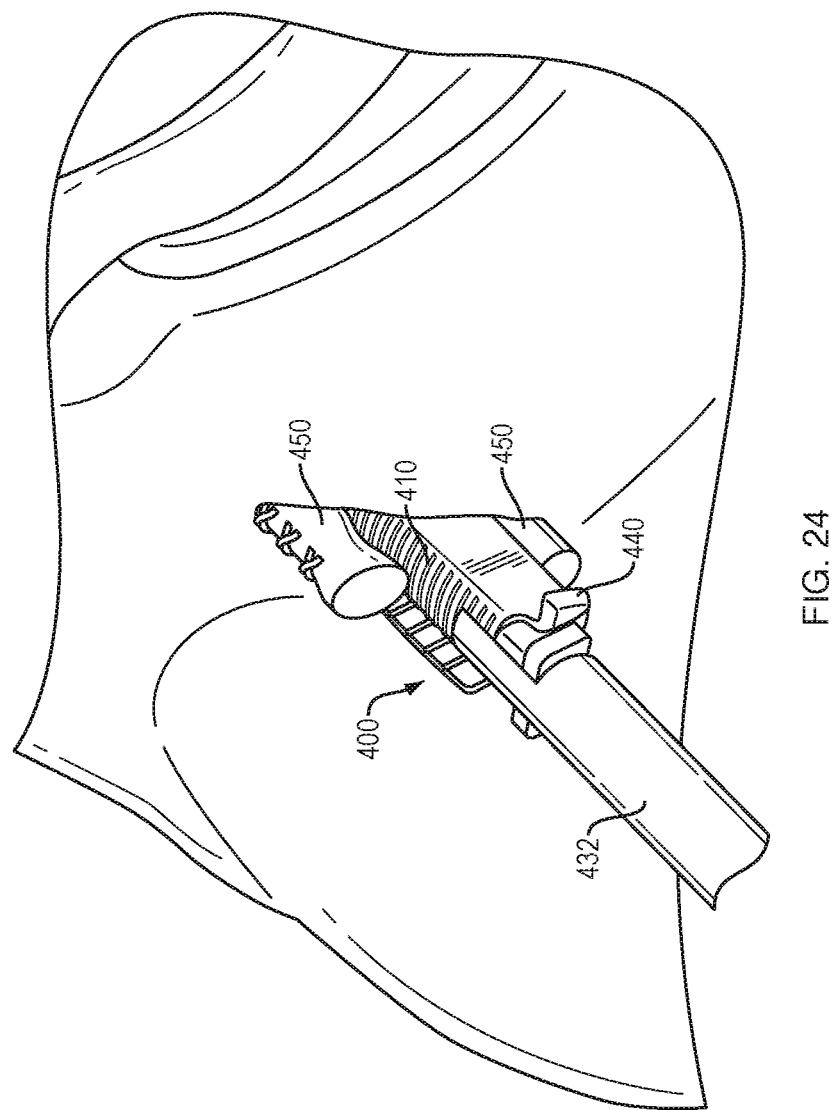
FIGS. 24-27 illustrate installing another fixation device in the tibia to secure a tissue graft thereto.
Figure 25:
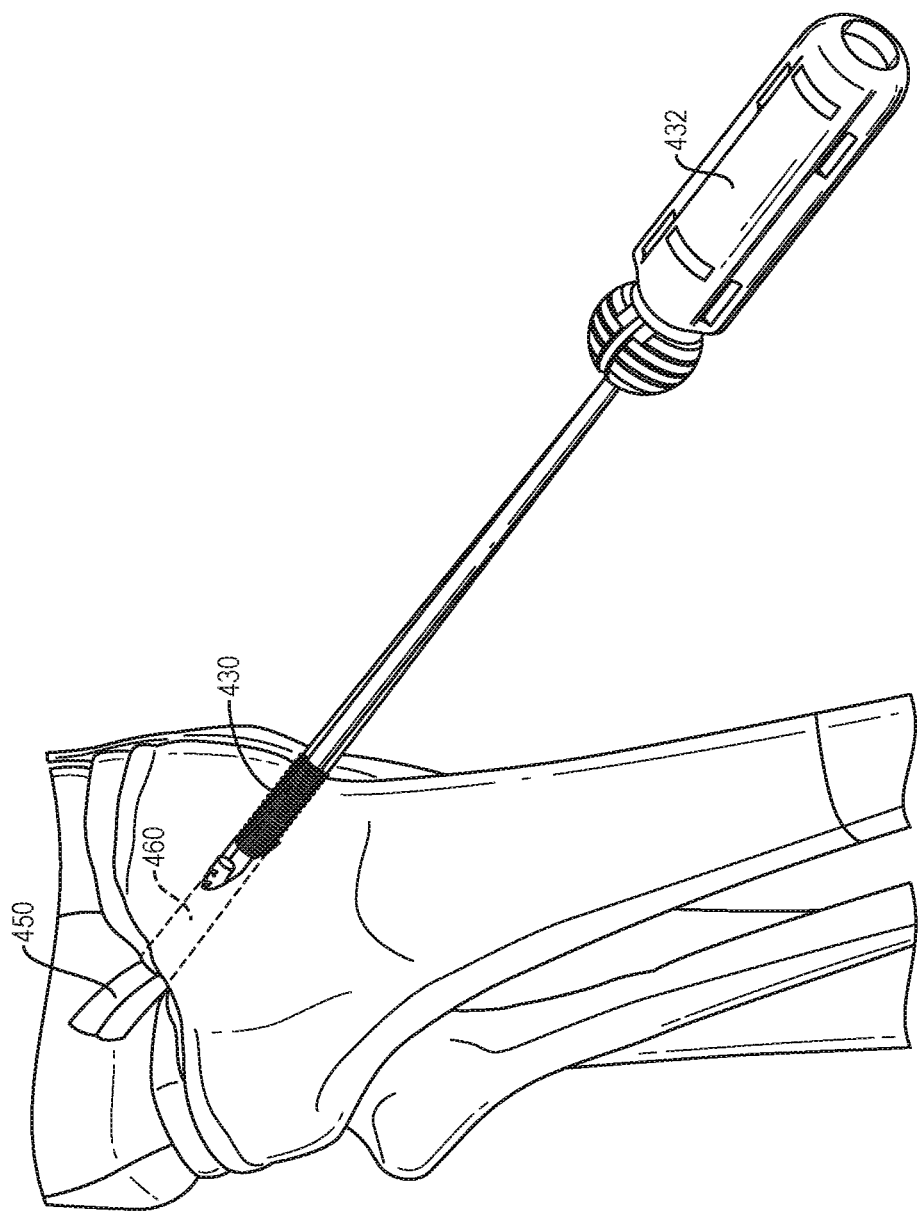
Figure 26:
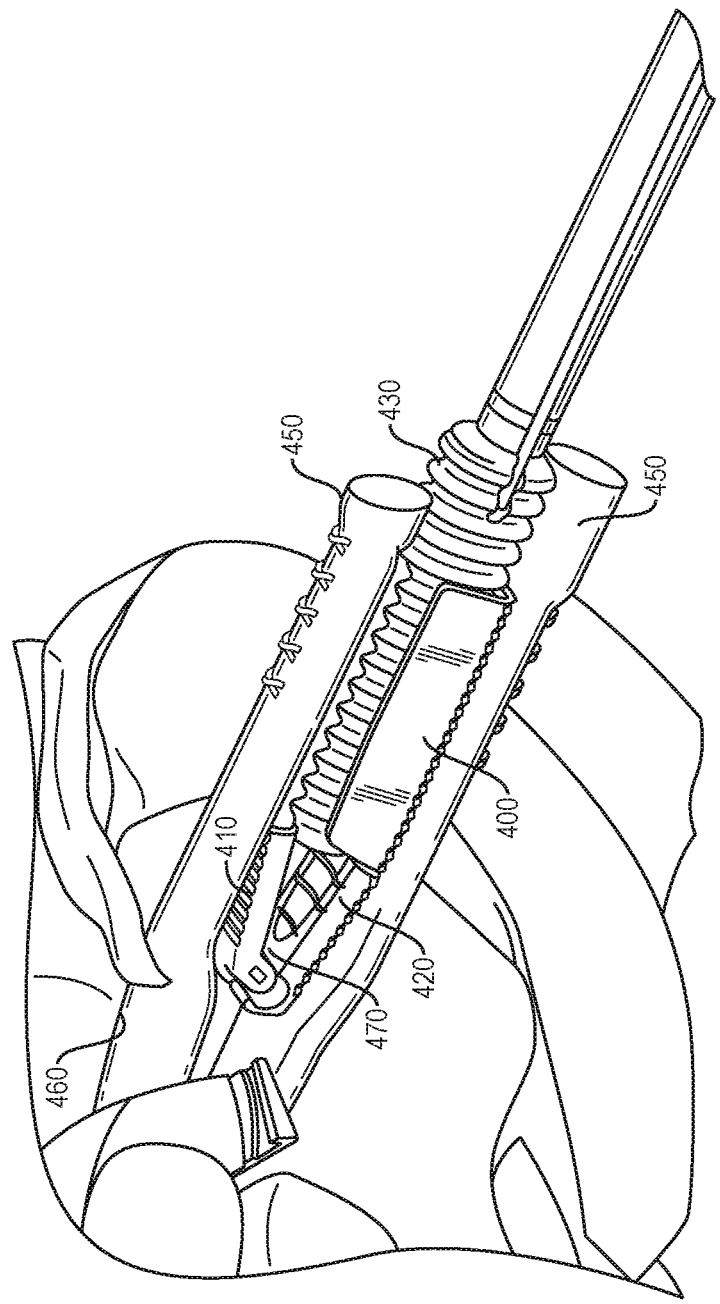
Figure 27:
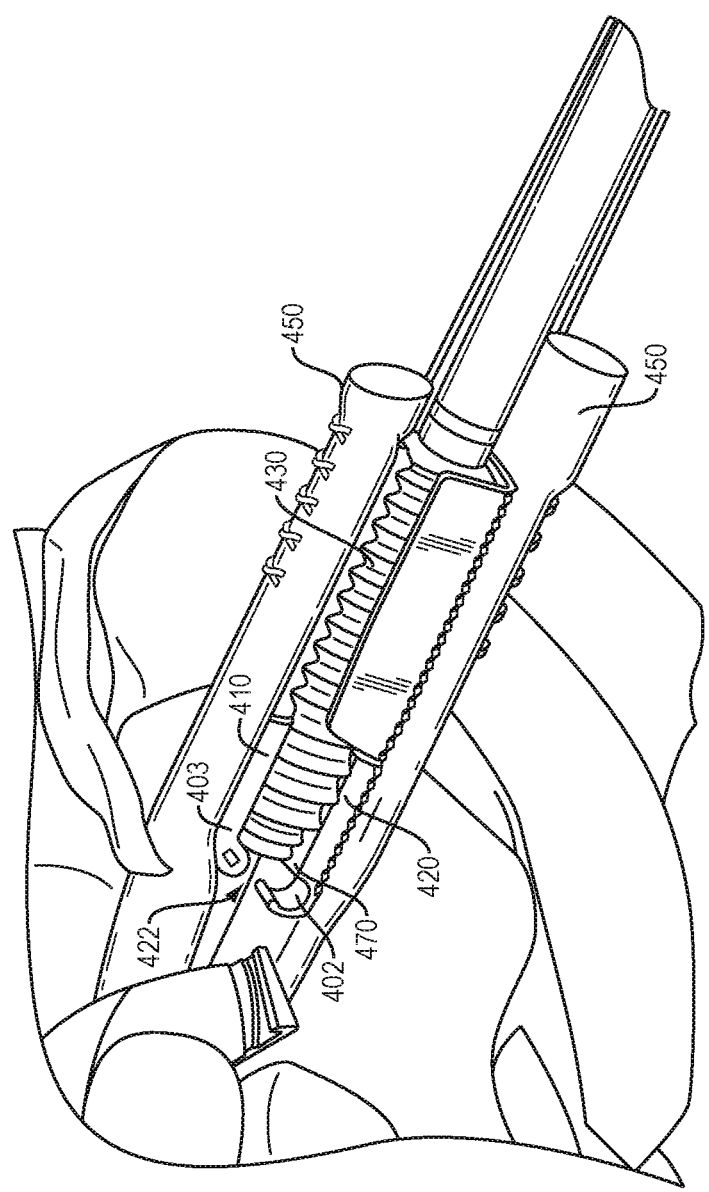

FIGS. 24-27 illustrate sequentially deployment of the tissue fixation device 400 into a bone hole to secure tissue therein. With reference first to FIG. 24, an insertion tool 432 is shown inserting fixation device 400 into a bone hole. The tissue fixation device 400 is inserted into the bone hole until nub 440 abuts an exterior bone surface. The nub 440 limits the depth of engagement. Next, with reference to FIG. 25, screw 430 is inserted into the tissue fixation device 400 with the insertion tool 432 to lock the soft tissue 450 in the bone hole 460. FIG. 26 shows sheath members 410, 420 separated by a seam 470. The sheath members 410, 420 are rotated away from one another to compress the legs of the tissue 450 against the bone hole 460. In embodiments, the legs of the tissue 450 are positioned against the wide regions of a non-circular bone hole 460. FIG. 27 shows the distal hinge 422 separated into discrete elements 402, 403. Seam 470 has been enlarged with the insertion of the screw 430. Notably, the distal position of the hinge 422 (and the manner in which the hinge elements cooperate with one another) causes the sheath members 410, 420 to apply force in a direction substantially perpendicular to the tissue/bone wall, and to avoid shearing or twisting the legs of the tissue 450.

Figure 28:
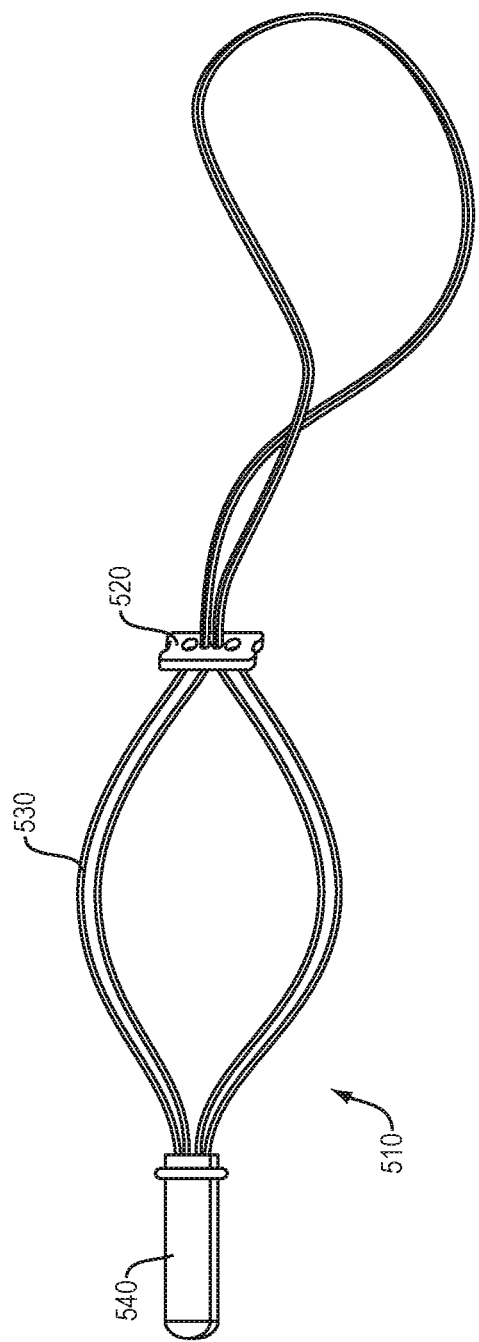
FIG. 28 illustrates another fixation device comprising a sleeve, interference screw, and cortical button connected to the sleeve via suture.

Optionally, a redundant or back-up fixation device, such as, for example, the cortical button 520 shown in FIG. 28, may be tethered with suture a 530 to the tissue fixation device 540 to form an enhanced tissue fixation construct 510. The cortical button 520 is operated and installed against the surface of the bone as described above in connection with FIGS. 12-15 to bolster the fixation of the tissue fixation device 540 in the bone tunnel.

Figure 29:
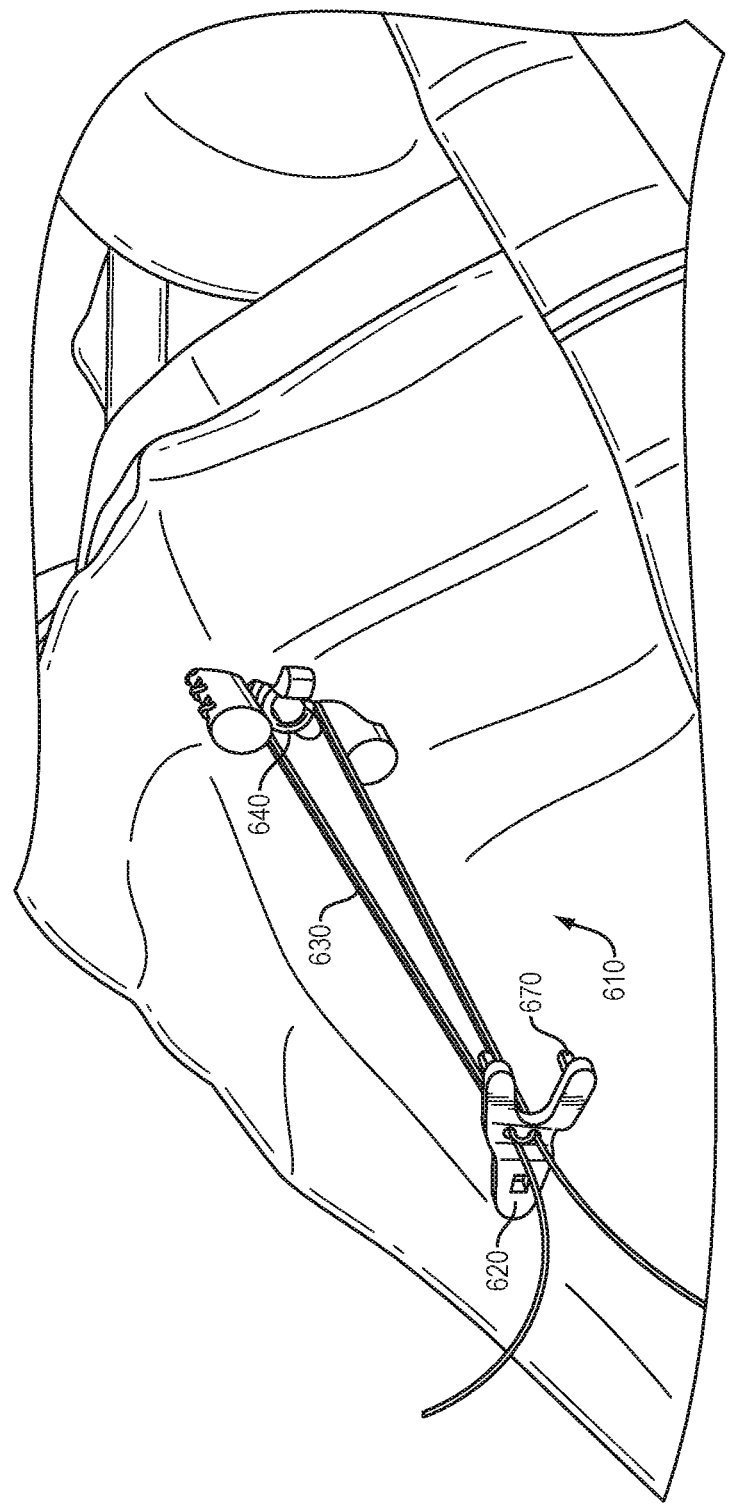
FIGS. 29-30 illustrate installation of another cortical button to enhance fixation of tissue grafts to the tibia.
Figure 30:
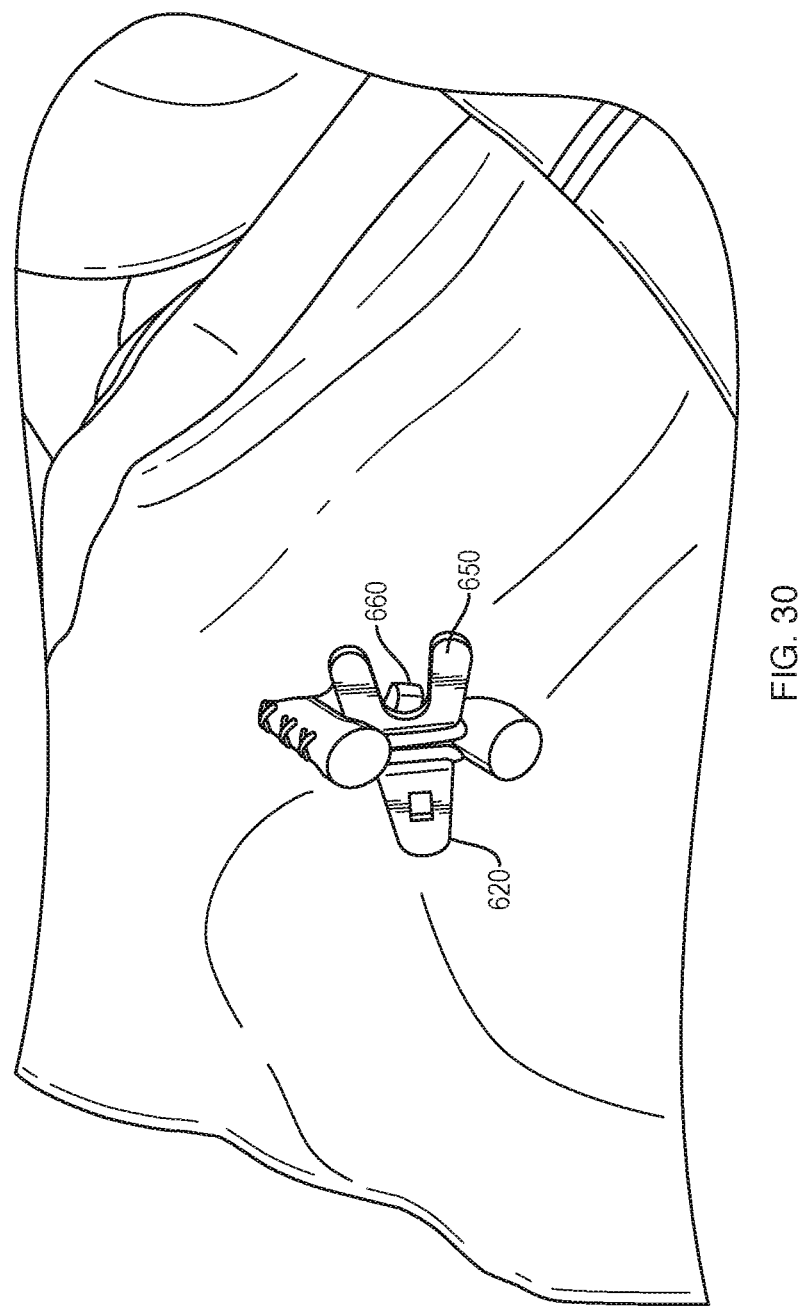

FIG. 29 illustrates another cortical button 620 similar to that described above except that cortical button 620 is tethered by the suture 630 to the screw 640 instead of the tissue fixation device 610. The cortical button 620 may comprise at least one barb 670 or similar feature to engage the cortical surface of the bone. With reference to FIG. 30, cortical button 620 is registered or aligned across the neck or minor axis ($A_{minor}$) (FIG. 22) of the bone hole (not shown). A recess 650 in the cortical button 620 permits the nub 660 to nest within the plane of the cortical button 620. This registration between the components creates a low profile on the exterior surface of the bone and is desired post operation to improve the cosmetic appearance of the tissue repair.

While preferred embodiments of this disclosure have been shown and described, modifications thereof can be made by one skilled in the art without departing from the scope or teaching herein. The embodiments described herein are exemplary only and are not intended to be limiting. Because many varying and different embodiments may be made within the scope of the present inventive concept, including equivalent structures, materials, or methods hereafter thought of, and because many modifications may be made in the embodiments herein detailed in accordance with the descriptive requirements of the law, it is to be understood that the details herein are to be interpreted as illustrative and not in a limiting sense.

We claim:

1. A fixation device for securing a soft tissue in a bone hole comprising:
   a screw comprising external surface features;
   a sheath comprising a proximal end, a distal end, and a lumen extending from the proximal end towards the distal end, the lumen comprising internal surface features to receive and engage the external surface features of the screw, said sheath further comprising:
   a first sheath component comprising a first side wall and a first lateral wall;
   a second sheath component non-integrally formed with the first sheath component, and the second sheath component comprising a second side wall and a second lateral wall;

wherein the lumen is defined by the first side wall, the second side wall, the first lateral wall, and the second lateral wall;

wherein the first sheath component and the second sheath component are in hinged engagement about a lateral axis at the distal end of the sheath, enabling the first lateral wall to incrementally pivot from the second lateral wall about the lateral axis according to the depth that the screw is inserted into the lumen of the sheath; and, wherein the first side wall and the second side wall comprise internally disposed vertical guides.

2. The fixation device of claim 1 wherein the screw has an outer diameter that decreases from the proximal end to the distal end.

3. The fixation device of claim 1 wherein the lumen has an inner diameter that decreases from the proximal end to the distal end.

4. The fixation device of claim 1 wherein the first side wall and the second side wall are substantially flat.

5. The fixation device of claim 1 wherein the first side wall and the second side wall are substantially parallel.

6. The fixation device of claim 1 wherein the first lateral wall and second lateral wall comprise curved internal surfaces.

7. The fixation device of claim 1 wherein the first lateral wall and the second lateral wall each have an exterior surface to contact the tissue, and the exterior surface comprises surface features to grip the tissue when the sheath is deployed.

8. The fixation device of claim 1 further comprising a nub member at the proximal end of the sheath to engage an exterior surface of the bone, thereby limiting the depth of insertion of the sheath into the bone hole.

9. A fixation device for securing a soft tissue in a bone hole comprising:
 a screw;
 a sheath comprising a first part, a second part non-integral to the first part, a proximal end, a distal end, a lumen extending from the proximal end to the distal end and adapted to accept the screw, and a hinge rotatably interlocking the first part to the second part at the distal end;
 a cortical button tethered to a proximal end of at least one of the screw and the sheath, said cortical button comprising at least one barb to engage the cortical surface of the bone;
 wherein the lumen comprises a longitudinal axis extending from a proximal end to the distal end of the sheath, and a cross section comprising a lateral dimension and a vertical dimension;
 wherein the sheath further comprises a first low profile configuration when the sheath is inserted into the bone hole, and a second high profile configuration when the sheath is deployed in the bone hole to lock the tissue therein; and
 wherein the second high profile configuration is assumed when the screw is inserted into the lumen causing the lumen to substantially enlarge in the vertical dimension while the lateral dimension remains substantially the same, thereby causing an exterior surface of the sheath to be urged against the tissue and locking the tissue in the bone hole.

10. The fixation device of claim 9 wherein the hinge comprises substantially rigid discrete separable elements, thereby causing the first part of the sheath to disengage from the second part of the sheath when the screw is inserted a predetermined depth.

11. The fixation device of claim 9 wherein each of the first part and the second part of the sheath comprises a vertical wall.

12. The fixation device of claim 11 wherein a portion of each vertical wall extends beyond the vertical dimension of the sheath when the sheath is in the first low profile configuration.

13. The fixation device of claim 9 wherein the cortical button further includes an interlocking feature to register with a corresponding interlocking feature present on the sheath.

* * * * *